US00PP19738P2

(12) United States Plant Patent
Fountain

(10) Patent No.: US PP19,738 P2
(45) Date of Patent: Feb. 17, 2009

(54) ***ACALYPHA* PLANT NAMED 'SIZZLE SCISSORS'**

(50) Latin Name: *Acalypha godseffiana*
Varietal Denomination: Sizzle Scissors

(75) Inventor: Birdie L. Fountain, Valley Center, CA (US)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/151,157

(22) Filed: May 2, 2008

(51) Int. Cl.
*A01H 5/00* (2006.01)

(52) U.S. Cl. ..... Plt./373
(58) Field of Classification Search ..... Plt./373
See application file for complete search history.

(56) References Cited

U.S. PATENT DOCUMENTS

PP4,475 P * 11/1979 Huey ..... Plt./373

* cited by examiner

*Primary Examiner*—Wendy C. Haas
(74) *Attorney, Agent, or Firm*—C. A. Whealy

(57) ABSTRACT

A new and distinct cultivar of *Acalypha* plant named 'Sizzle Scissors', characterized by its compact, rounded, upright and outwardly spreading plant habit; vigorous growth habit; freely branching habit; and deeply and irregularly crenate leaves that are green, pink and red purple in color.

1 Drawing Sheet

Botanical designation: *Acalypha godseffiana.*
Cultivar denomination: 'Sizzle Scissors'.

BACKGROUND OF THE INVENTION

The present invention relates to a new and distinct cultivar of *Acalypha* plant, botanically known as *Acalypha godseffiana,* and hereinafter referred to by the name 'Sizzle Scissors'.

The new *Acalypha* originated is a naturally-occurring branch mutation of a proprietary selection of *Acalypha godseffiana* 'Firestorm', not patented. The new *Acalypha* was discovered and selected by the Inventor on a single plant within a population of plants of 'Firestorm' in a controlled greenhouse environment in Bonsall, Calif. in 2003.

Asexual reproduction of the new *Acalypha* by vegetative cuttings in a controlled greenhouse environment in Bonsall, Calif. since 2004, has shown that the unique features of this new *Acalypha* are stable and reproduced true to type in successive generations.

SUMMARY OF THE INVENTION

The cultivar Sizzle Scissors has not been observed under all possible environmental conditions. The phenotype may vary somewhat with variations in environment such as temperature and light intensity, without, however, any variance in genotype.

The following traits have been repeatedly observed and are determined to be the unique characteristics of 'Sizzle Scissors'. These characteristics in combination distinguish 'Sizzle Scissors' as a new and distinct cultivar of *Acalypha:*

1. Compact, rounded, upright and outwardly spreading plant habit.
2. Vigorous growth habit.
3. Freely branching habit.

4. Deeply and irregularly crenate leaves that are green, pink and red purple in color.

Plants of the new *Acalypha* differ from plants of the parent, 'Firestorm', in the following characteristics:

1. Plants of the new *Acalypha* are more compact than plants of 'Firestorm'.
2. Plants of the new *Acalypha* have narrower and more crenate leaves than plants of 'Firestorm'.

Plants of the new *Acalypha* can be compared to plants of the *Acalypha* 'Dallas', disclosed in U.S. Plant Pat. No. 4,475. In side-by-side comparisons conducted in Bonsall, Calif., plants of the new *Acalypha* differed from plants of 'Dallas' in the following characteristics:

1. Plants of the new *Acalypha* had more crenate leaves than plants of 'Dallas'.
2. Plants of the new *Acalypha* had green, pink and red purple-colored leaves whereas than plants of 'Dallas' had yellow and green-colored leaves.

BRIEF DESCRIPTION OF THE PHOTOGRAPHS

The accompanying photographs illustrate the overall appearance of the new *Acalypha.* These photographs show the colors as true as it is reasonably possible to obtain in colored reproductions of this type. Colors in the photographs may differ slightly from the color values cited in the detailed botanical description which accurately describe the colors of the new *Acalypha.*

The photograph at the bottom of the sheet comprises a side perspective view of three typical plants of 'Sizzle Scissors'.

The photograph at the top of the sheet is a close-up view of a typical plant of 'Sizzle Scissors'.

DETAILED BOTANICAL DESCRIPTION

In the following description, color references are made to The Royal Horticultural Society Colour Chart, 1995 Edition, except where general terms of ordinary dictionary significance are used. The aforementioned photographs, and following observations and measurements describe plants grown in Bonsall, Calif. during the autumn in an outdoor nursery in one-gallon containers and under conditions and practices which approximate those generally used in commercial *Acalypha* production. During the production of the plants, day temperatures ranged from 16° C. to 38° C. and night temperatures ranged from 13° C. to 21° C. Measurements and numerical values represent averages for typical plants. Plants were 18 weeks old when the photographs and description were taken and were pinched one time. The following description describes single plants.

Botanical classification: *Acalypha godseffiana* 'Sizzle Scissors'.

Parentage: Naturally-occurring branch mutation of *Acalypha godseffiana* 'Firestorm', not patented.

Propagation:

*Type.*—By vegetative cuttings.

*Time to initiate roots.*—About three weeks.

*Time to produce a rooted young plant.*—About four weeks.

*Root description.*—Fibrous, medium in thickness; white in color.

*Rooting habit.*—Freely branching; dense.

Plant description:

*Plant habit.*—Compact, rounded, upright and outwardly spreading plant habit. Freely branching habit with about five to six primary lateral branches per plant; pinching enhances lateral branch development; dense and bushy plant habit. Vigorous growth habit.

*Plant height.*—About 24 cm.

*Plant diameter.*—About 21 cm.

Lateral branch description:

*Length.*—About 21 cm.

*Diameter.*—About 2.5 mm.

*Internode length.*—About 1.6 cm.

*Strength.*—Strong.

*Texture.*—Pubescent.

*Color, developing stems.*—Close to 145A.

*Color, mature stems.*—Close to 195A.

Foliage description:

*Arrangement.*—Towards the base of the plant, alternate; towards the apex of the plant, whorled; simple.

*Length.*—About 6 cm.

*Width.*—About 1.3 cm to 1.6 cm.

*Shape.*—Roughly elliptical and deeply crenate; twisting.

*Apex.*—Rounded to broadly acute.

*Base.*—Attenuate.

*Margin.*—Deeply crenate.

*Texture, upper and lower surfaces.*—Sparsely pubescent.

*Venation pattern.*—Pinnate; reticulate.

*Color.*—Developing foliage, upper surface: Close to 147A. Developing foliage, lower surface: Close to 147B. Fully expanded foliage, upper surface: Close to 147A; lobes, close to 50C; margins, close to 59B; venation, close to 183A. Fully expanded foliage, lower surface: Close to 147B; lobes, close to 50C; venation, close to 183B.

*Petiole.*—Length: About 2.7 cm. Diameter: About 1.5 mm. Texture, upper and lower surfaces: Sparsely pubescent. Color, upper surface: Close to 177C. Color, lower surface: Close to 182B.

Flower description: Flower development has not been observed on plants of the new *Acalypha*.

Garden performance: Plants of the new *Acalypha* have been observed to tolerate wind, rain and temperatures ranged from 5° C. to 38° C.

Pathogen/pest resistance: Plants of the new *Acalypha* have not been observed to be resistant to pathogens and pests common to *Acalyphas*.

It is claimed:

1. A new and distinct *Acalypha* plant named 'Sizzle Scissors' as illustrated and described.

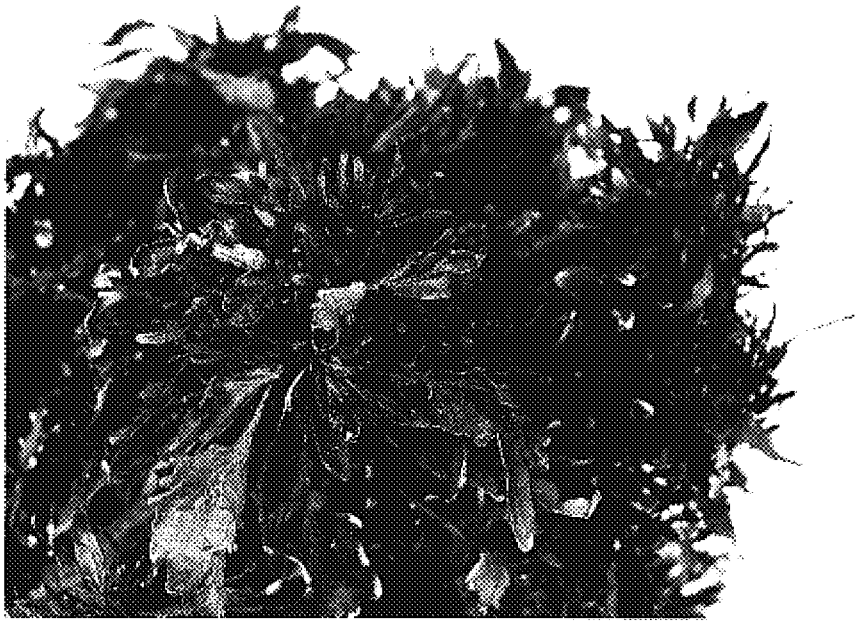
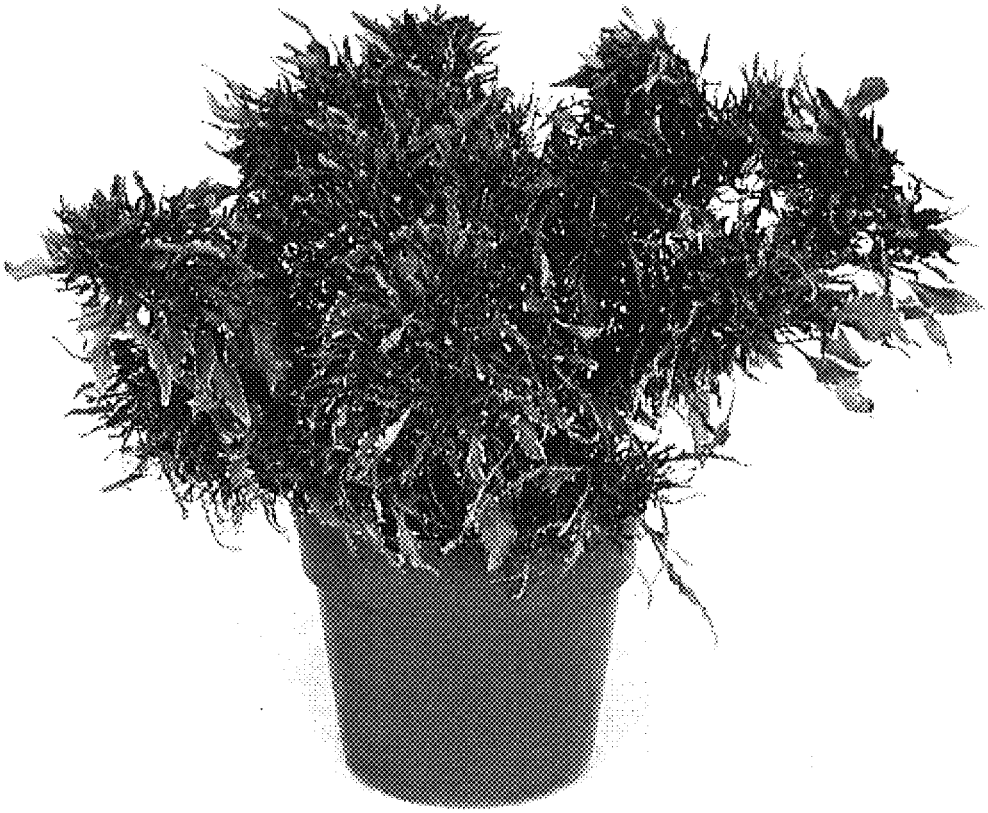

* * * * *